United States Patent [19]

Müller et al.

[11] Patent Number: 5,380,324

[45] Date of Patent: Jan. 10, 1995

[54] IMPLANTABLE DEVICE FOR STRAIGHTENING AND FIXING VERTEBRAE

[75] Inventors: Walter Müller, Voehringen; Georg Piotrowski, Oberndorf, both of Germany

[73] Assignee: Pina Vertriebs AG, Neuhausen 2/SH, Germany

[21] Appl. No.: 99,618

[22] Filed: Jul. 30, 1993

[51] Int. Cl.⁶ .......................................... A61B 17/58
[52] U.S. Cl. .................................................... 606/61
[58] Field of Search ................ 606/61, 73, 59, 60, 606/69; 623/17

[56] References Cited

U.S. PATENT DOCUMENTS

| 4,611,581 | 9/1986 | Steffee ....................... 606/73 X |
| 4,771,767 | 9/1988 | Steffee ....................... 606/61 X |
| 4,773,402 | 9/1988 | Asher et al. ................. 606/61 |
| 5,057,109 | 10/1991 | Olerud. |

FOREIGN PATENT DOCUMENTS

| 2651992 | 3/1991 | France. |
| 8711192 | 11/1987 | Germany. |
| 3807346 | 6/1989 | Germany. |
| 1417869 | 8/1988 | U.S.S.R. ..................... 606/69 |

OTHER PUBLICATIONS

"Vitallium Surgical Appliances", Bone Plates, Mar. 1948, p. 8.

Primary Examiner—Tamara L. Graysay
Attorney, Agent, or Firm—McGlew & Tuttle

[57] ABSTRACT

An implant for the spinal column for fixing the vertebrae, especially the cervical vertebra, on the anterior side, i.e., on the side of the esophagus, wherein the implant has screw holes for screwing together with the vertebra and has a multi-component design, and has at least two mounting plates, which are provided with at least two screw holes. The mounting plates are connected by an articulated bearing each to a spindle having right-hand and left-hand, self-locking threads with an angular shaft piece for actuating the spindle, wherein the mounting plates have a ribbed area on the side facing the vertebral bone W. The articulated bearing includes a bearing bush extending outwardly from each mounting plate and a bearing pin which has a threaded hole for engaging the spindle. The bushing has a hole allowing the spindle to pass through the bearing bush wherein pin is moveable within the bearing bush.

8 Claims, 6 Drawing Sheets

FIG. 11 is an implant for the spinal column for fixing the vertebrae, especially the cervical vertebrae, on the anterior side, i.e., on the esophageal side wherein the implant has screw holes for screwing to the vertebrae.

IMPLANTABLE DEVICE FOR STRAIGHTENING AND FIXING VERTEBRAE

FIELD OF THE INVENTION

The present invention pertains to an implant for the spinal column for fixing the vertebrae, especially the cervical vertebrae, on the anterior side, i.e., on the esophageal side wherein the implant has screw holes for screwing to the vertebrae.

BACKGROUND OF THE INVENTION

An implant that has become known as an example is essentially a metal band, on which lateral straps are arranged, and both the metal band and the straps have screw holes, which are provided for accommodating bone screws. These metal bands are available in different lengths to ensure that they can be selected corresponding to the physical conditions of a given patient.

The vertebrae are fixed with such band-like implants by screwing the implant onto a vertebra, after a so-called bed for the implant has been created on the surface of the vertebra by, e.g., milling off the vertebral bone W in order to prepare a corresponding support surface for the band-like implant. A bed also must be formed on the adjacent vertebra to be fixed in order to subsequently screw this vertebra together with the band-like implant in the medically necessary position of the vertebra.

The disadvantage of such a band-like implant is that these procedures are to be performed under surgical conditions and they also require removal of the bone chips and the like, generated during the preparation of the two beds for the band-like implants. Moreover, the heads of the bone screws usually project from the vertebra together with the band-like implant, which leads to unpleasant, symptom-producing accompanying phenomena, especially in the area of the esophagus. In addition, it may be necessary, depending on the location of the vertebrae or their damage, to provide a washer between the band-like implant and one vertebra or both vertebrae in order to achieve a medically suitable fixation. In particular, the site at which the bone screws are screwed in cannot be selected solely based on medical criteria, because the screw holes in the band-like implant are permanently predetermined, as a result of which fixation cannot be always performed in a medically optimal manner. This may lead to a limitation of the medically necessary measures, especially in the case of osteoporosis, because the location of the screw holes must be selected in this case so as to ensure that they will not break out. There also is a risk of breaking out especially in the case of screw holes in peripheral zones of the vertebra, which frequently must be used in the case of the band-like implant, because precisely the screw holes are permanently predetermined by their distances on the band-like implant. Moreover, it is necessary to keep in stock the different, medically necessary sizes of band-like implant.

SUMMARY AND OBJECTS OF THE INVENTION

The object of the present invention is to eliminate the disadvantages of prior-art band-like implants and to provide an implant that makes possible the medically conformal fixation or ventral cervical stabilization, with possibly optimal selection of the position of the bone screws, if possible, also to avoid hindrances for the patient, e.g., due to a reduction of the esophageal cross section, etc. It is also desirable to eliminate the need for additional auxiliary means, such as washers, etc., to achieve the medically optimal position. The amount of preparation of the vertebral bone for installing the implant shall be as small as possible, or the need for such preparation should be eliminated altogether.

This object can be attained by the implant according to the present invention for the spinal column for fixing the vertebrae, especially the cervical vertebrae, wherein the implant is of a multicomponent design and has at least two mounting plates. The mounting plates are provided with screw holes and are connected, by means of an articulated bearing each, to a spindle. The spindle is provided with left hand and right hand threads with an angular shaft piece for actuating the spindle. The mounting plates have a ribbed area on the side facing the vertebral bone.

The mounting plate of a first variant is designed as a kidney-shaped, arched plate. With the mounting plate, the articulated bearing is made in one piece at one of its ends.

The mounting plate of a second variant is designed as a kidney-shaped, arched plate having a holding tab. The articulated bearing with the mounting plate is made in one piece at one of its ends.

The articulated bearing may be formed of at least one bearing bush which has a spindle hole for the passage of the spindle, essentially at right angles to the longitudinal extension of the mounting plate. The bearing bush has a cylindrical inner wall. The articulate bearing also includes a cylindrical bearing pin which can be inserted into the bearing bush. The bearing pin is provided with a hole with internal threads for engaging the spindle (for screwing in the spindle).

The articulated bearing may also be formed with the bearing bush having the spindle hole for passage of the spindle essentially at right angles to the longitudinal extension of the mounting plate and the inner cylindrical wall. The bearing pin may be a double truncated cone-shaped pin which can be inserted into the bearing bush and which again has a hole with internal threads for screwing in the spindle.

The articulated bearing may also include the bearing bush with the spindle hole and cylindrical inner wall and also a barrel-shaped bearing pin which can be inserted into the bearing bush and has a hole with internal threads for screwing in the spindle. The bearing pin may also be spherical.

The spindle may be permanently screwed with its free ends into the bearing pin and may be provided with a pinched area acting as a securing means against screwing out at the threaded end.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

STATE OF THE ART

Figure 1:
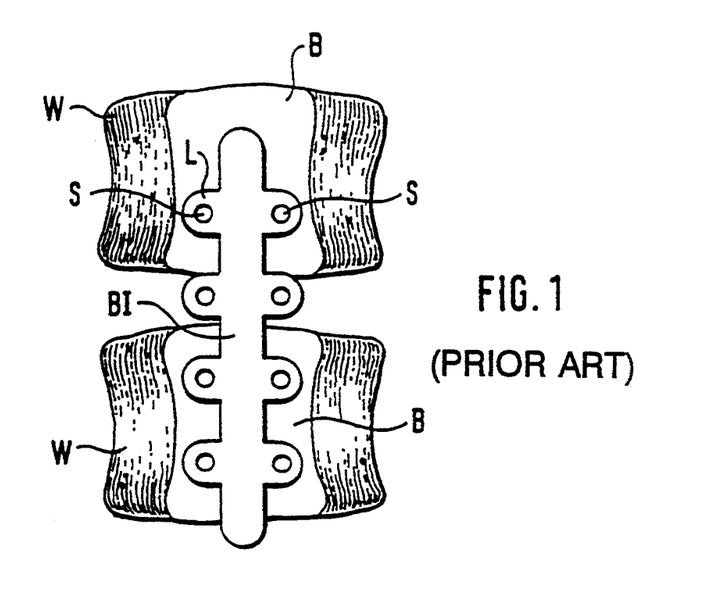
FIG. 1 is a front view of a band-like implant according to the state of the art.
Figure 2:
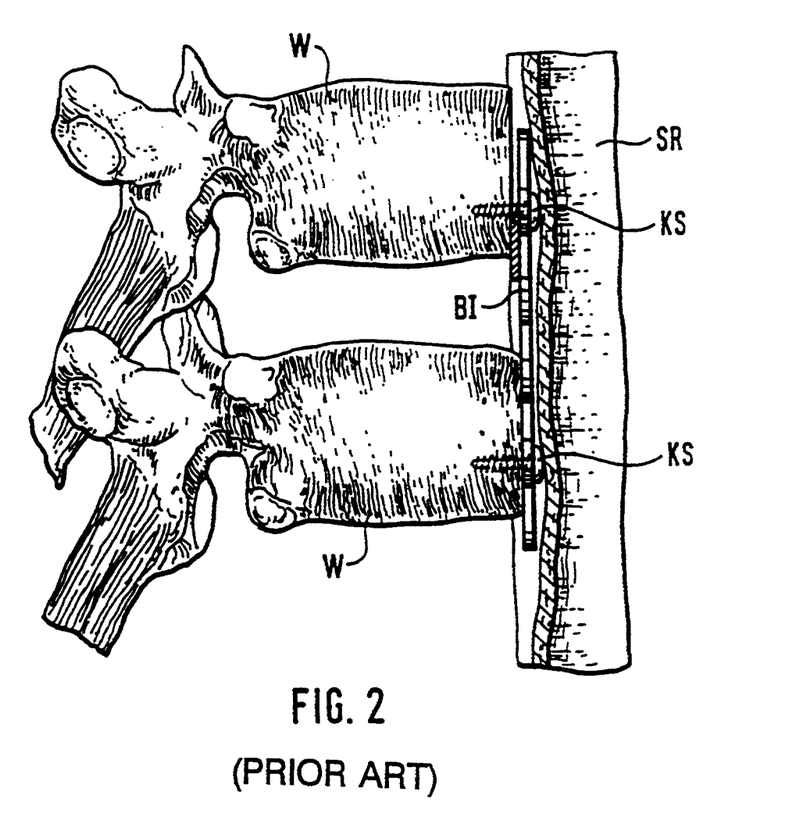
FIG. 2 is a side view of a band-like implant according to the state of the art.
Figure 3:
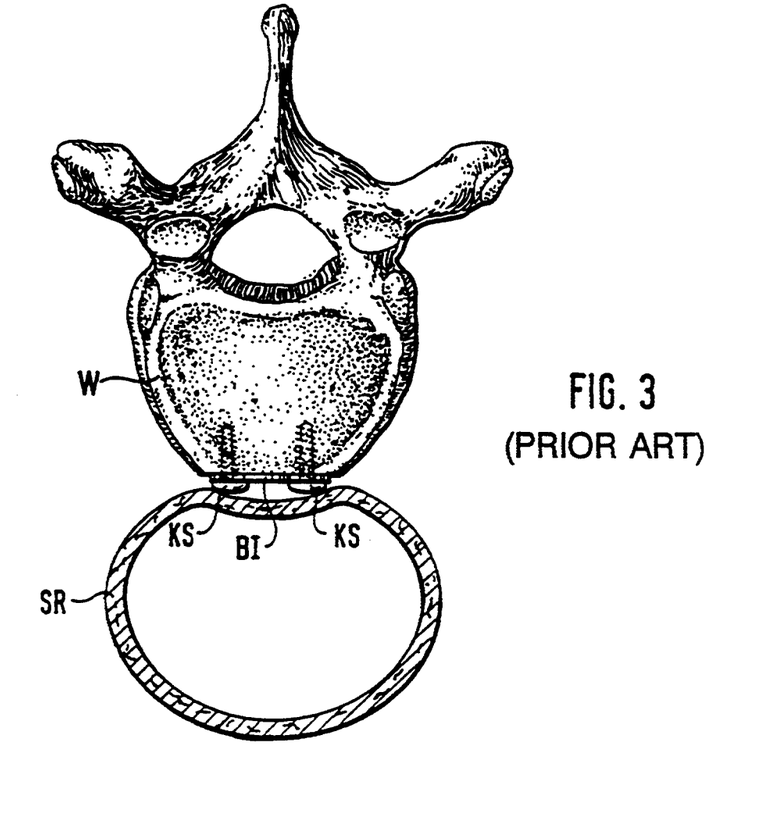
FIG. 3 is a top view of a band-like implant according to the state of the art.

The implant BI according to the state of the art shown in FIGS. 1, 2 and 3 is essentially a metal band, on which lateral straps L are arranged, and both the metal band and the straps L have screw holes S, which are provided for accommodating bone screws KS. The screw holes S and the straps L having the screw holes are arranged at fixed distances, and the metal bands are available in different lengths, so that they can be selected corresponding to the patient's physical conditions. Such a band-like implant BI requires a bed B on the vertebral bone W in order for it to be able to be mounted. The mounting is performed by screwing the band-like implant onto the vertebral bone W. The bed B is prepared by, e.g., milling off the vertebral bone W. A bed B must also be formed on the adjacent vertebral bone W to be fixed in order to subsequently screw together this vertebral bone W with the band-like implant BI in the medically necessary vertebral position. The narrowing of the esophagus SR caused by the band-like implant BI is shown in FIGS. 2 and 3. In addition, fixation with a band-like implant BI by means of a washer is shown in FIG. 2.

DETAILED DESCRIPTION OF THE PREFERRED EMBODIMENT

An implant 1 according to the present invention has at least two mounting plates 3.1, which are adjustably connected—by means of an articulated bearing 4 each, made in one piece with them—to a spindle 5 screwed into the said bearings.

Figure 7:
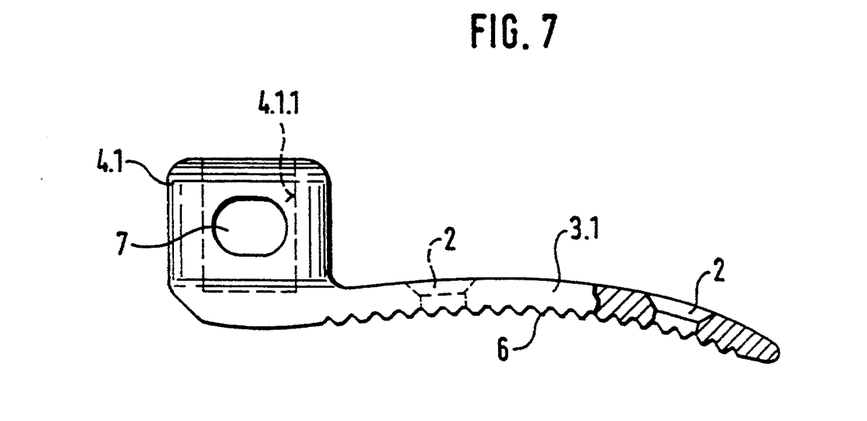
FIG. 7 is a top view of the mounting plate of a first variant of an implant according to the present invention.

A mounting plate 3.1 in a first variant is designed as a kidney-shaped, arched plate, with which the said articulated bearing 4 is made in one piece at one of its ends. It has, adjacent to the said articulated bearing 4, at least two screw holes 2, which are countersunk. On the side facing away frown the said articulated bearing 4, the said kidney-shaped, arched plate 3.1 has a ribbed area 6 (see FIG. 7), with which the force generated by the rotation of the vertebrae in relation to one another during movements of the patient, on the one hand, and that generated by the distortion of the vertebral bones W in relation to one another by means of the said spindle 5, on the other hand, can be absorbed better and not solely by the said bone screws in the said screw holes 2.

A mounting plate 3.2 in a second variant (FIG. 10) is designed just like the said mounting plate 3.1 of the first variant, but it additionally has a holding tab 3.3, which projects from it at right angles to its longitudinal extension and is used to hold a vertebral spacer that may have been inserted between the vertebrae or another, surgically necessary implant against sliding out of the space between the vertebrae.

Figure 11:
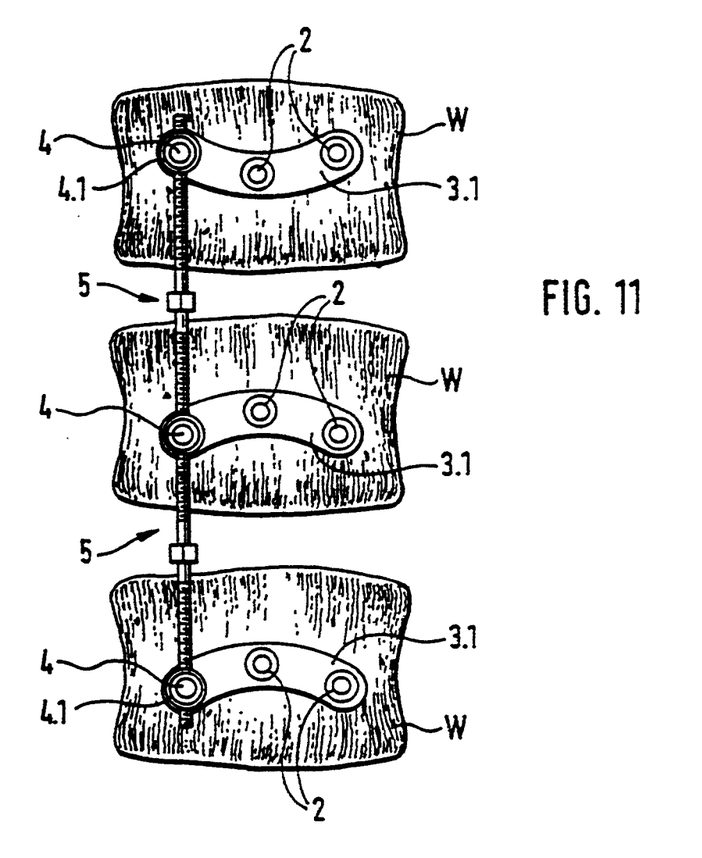
FIG. 11 is a front view of an implant according to the present invention (variant with a plurality of articulated bearings) mounted on three cervical vertebrae.

In a modified version (FIG. 11) of one of the two variants of the said mounting plate 3.1 or 3.2, it may suitably have two articulated bearings 4 arranged next to one another. Such a mounting plate with two articulated bearings 4 can be provided especially for connecting three vertebral bones W by attaching one mounting plate each of the first or second variant to the corresponding, adjacent vertebral bone W on both sides of the said double-articulated mounting plate and connecting the said two mounting plates of the first or second variant with the double-articulated mounting plate to a said spindle 5 each.

In a first embodiment, the said articulated bearing 4 consists of at least one bearing bush 4.1, which has a spindle hole 7 for the passage of the said spindle 5 essentially at right angles to the longitudinal extension of the said mounting plate 3.1, on the one hand, and a cylindrical inner wall 4.1.1, on the other hand, wherein a cylindrical bearing pin 4.3 can be inserted into the said bearing bush 4.1. This bearing pin 4.3 has a hole 4.4 with internal threads for screwing in the said spindle 5.

In a second embodiment, the said articulated bearing 4 consists of at least one said bearing bush 4.1, which has a said spindle hole 7 for the passage of the said spindle 5 essentially at right angles to the longitudinal extension of the said mounting plate 3, on the one hand, and a cylindrical inner wall 4.1.1, on the other hand, wherein a double truncated cone-shaped bearing pin 4.3.3 can be inserted into the said bearing bush 4.1. This bearing pin 4.3.3 has a said hole 4.4 with internal threads for screwing in the said spindle 5.

In a third embodiment, the said articulated bearing 4 consists of at least one said bearing bush 4.1, which has a said spindle hole 7 for the passage of the said spindle 5 essentially at right angles to the longitudinal extension of the said mounting plate 3, on the one hand, and a cylindrical inner wall 4.1.1, on the other hand, wherein a barrel-shaped bearing pin can be inserted into the said bearing bush 4.1. This bearing pin has a said hole with internal threads for screwing in the said spindle 5.

In a fourth embodiment, the said articulated bearing 4 consists of at least one bearing bush 4.1, which has a said spindle hole 7 for the passage of the said spindle essentially at right angles to the longitudinal extension of the said mounting plate 3, on the one hand, and an at least partially spherical inner wall (not shown) on the other hand, wherein a spherical bearing pin (not shown) can be inserted into the said bearing bush 4.1. This bearing pin would also have a hole with internal threads for screwing in the said spindle 5.

The said spindle 5 has left-hand and right-hand, self-locking threads, between which an angular shaft piece 5.1 is arranged for actuating the spindle, e.g., with a wrench or the like. In particular, the said spindle 5 may be screwed permanently with one of its free ends into a said bearing pin 4.3.3 each and have a pinched area acting as a means securing against screwing out at the corresponding thread end.

Figure 4:
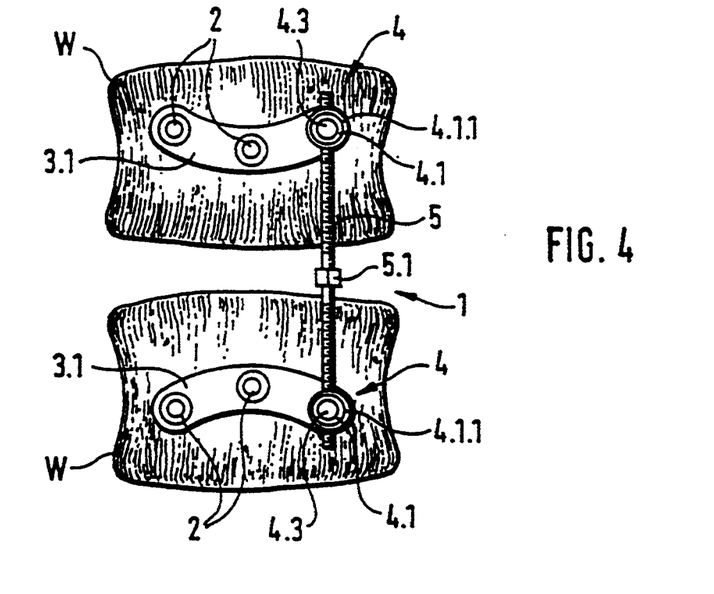
FIG. 4 is a front view of a first variant of an implant according to the present invention.
Figure 5:
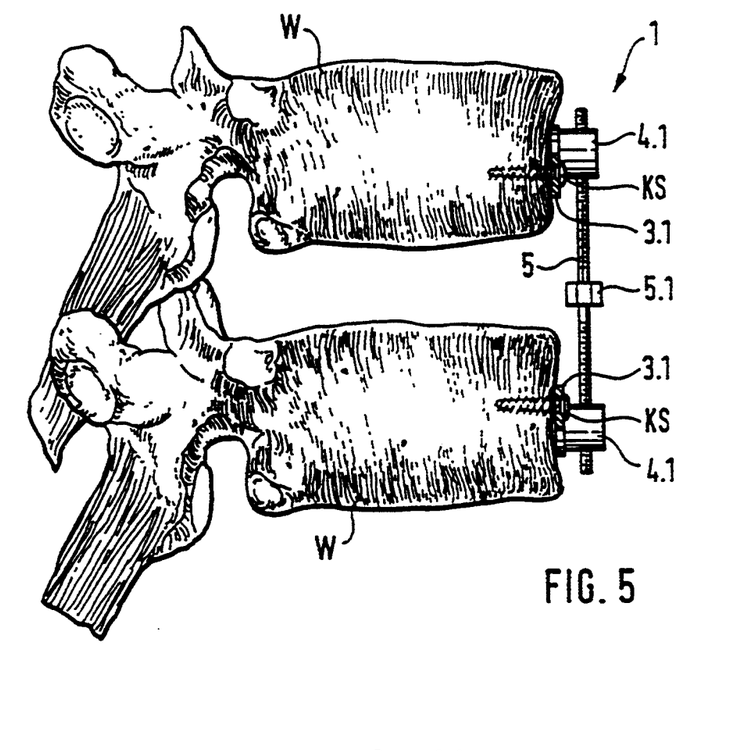
FIG. 5 is a side view of a first variant of an implant according to the present invention.
Figure 6:
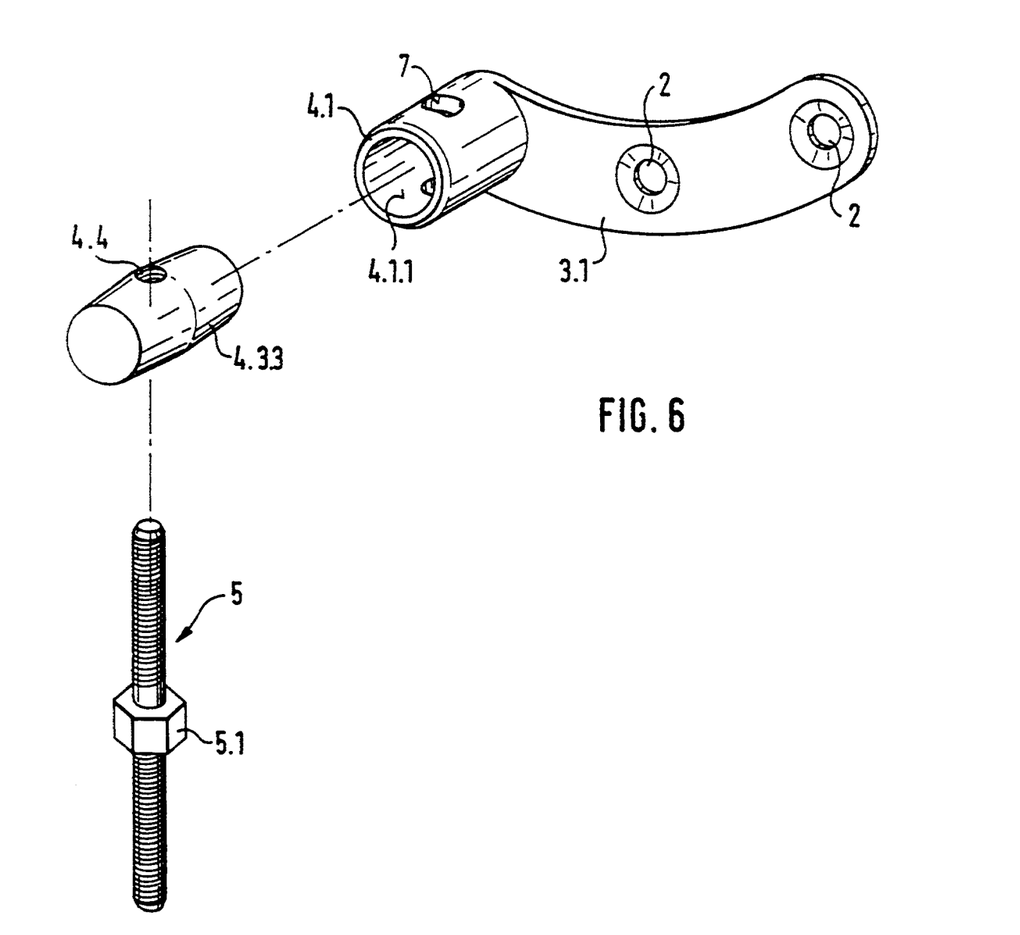
FIG. 6 is an axonometric, disassembled representation of a first variant of an implant according to the present invention.
Figure 10:
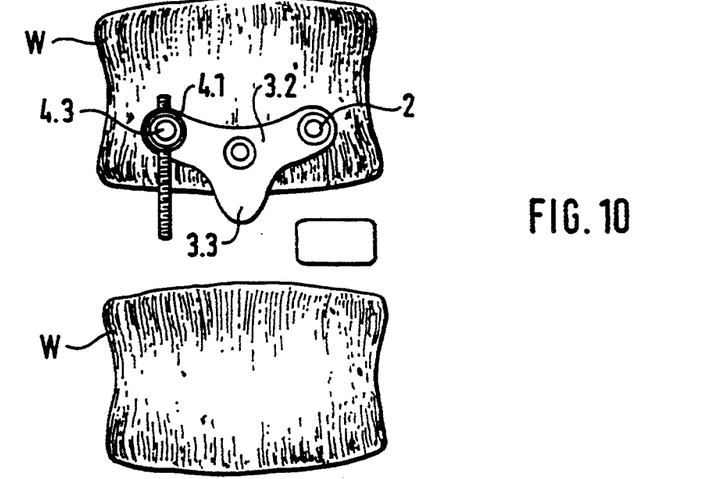
FIG. 10 is a front view of a second type of a mounting plate of an implant according to the present invention (second variant), which mounting plate is mounted on a cervical vertebra.

In the case of a compression or distraction (FIGS. 4, 5 and 6) of two adjacent vertebral bones W, one said mounting plate 3.1 in a first variant or a said mounting plate 3.2 in a second variant is screwed together with a corresponding first vertebral bone by means of said bone screws K. A said mounting plate 3.1 of a first variant or a said mounting plate 3.2 of a second variant is screwed together in the same manner with a corresponding second vertebral bone W by means of said bone screws K. The said two mounting plates 3 are subsequently connected by means of the said spindle 5, and the said two vertebral bones W are adjusted in relation to one another and fixed by rotating same the spindle 5. The said mounting plates 3 with the said articulated bearings 4 can be mounted on the said vertebral bones W somewhat to the side of the said esophagus SR, which leads to no or negligible impairment of the patient's ability to swallow. The said mounting plates 3.2 in a second variant are preferably used when other surgical aids, e.g., for supporting the said vertebral bones W, must also be used between the said vertebral bones W, but these aids must not leave the space between the said two vertebral bones W and can be held by the said mounting plate 3.2 of the second variant (FIG. 10).

In the case of a compression or distraction (FIG. 11) of three adjacent vertebral bones W, said mounting plates 3.1 or 3.2 of the first variant or of the second variant are mounted on the said two peripherally located vertebral bones W, whereas a mounting plate with two articulated bearings is screwed onto the said middle vertebral bone W. The said corresponding mounting plate 3 of the said adjacent vertebral bone W is adjusted and fixed with a said spindle 5 each on each side of the said middle vertebral bone W.

Figure 8:
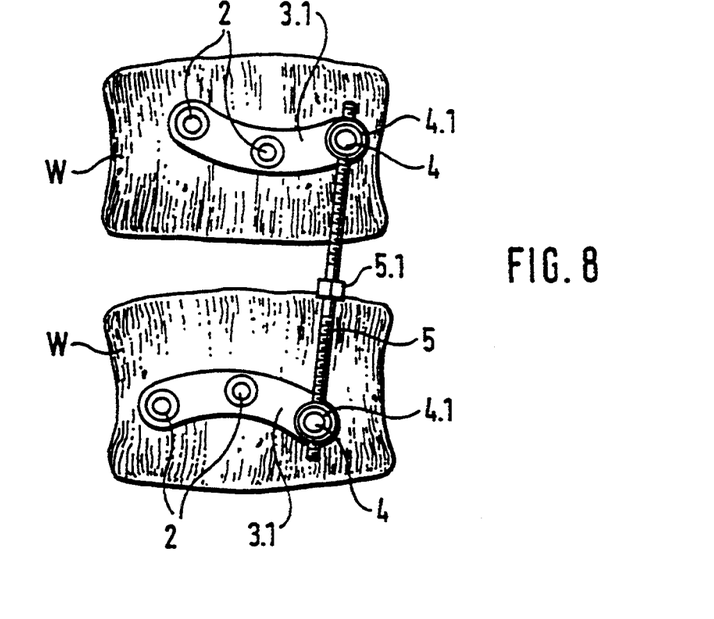
FIG. 8 is a front view of a mounting variant of a first variant of an implant according to the present invention.
Figure 9:
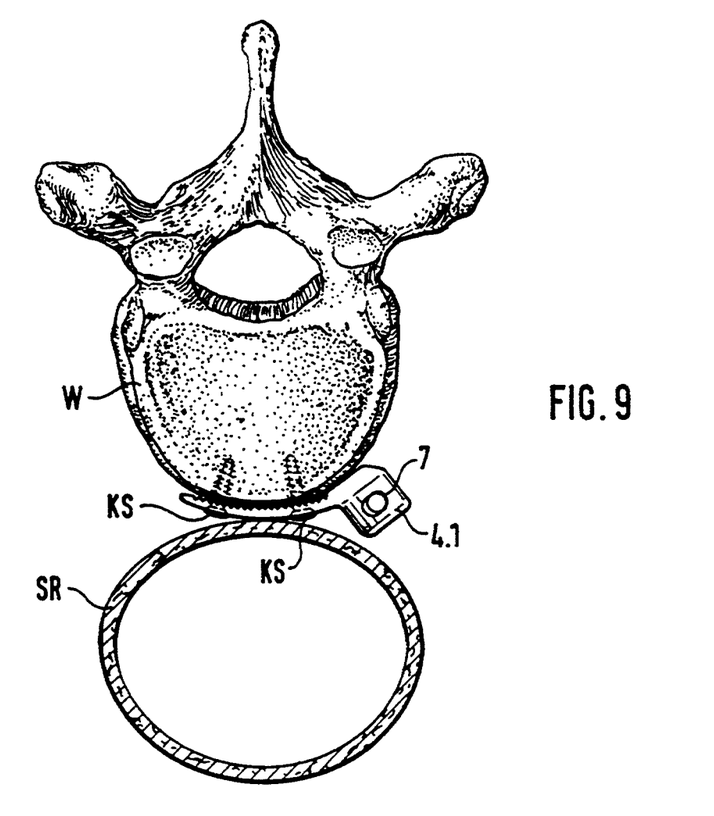
FIG. 9 is a top view of a first variant of an implant according to the present invention, mounted on a cervical vertebra.

However, it is also possible (FIG. 8) to mount the said two mounting plates 3 of said two adjacent vertebral bones W at any desired angle determined by the injury situation of the vertebrae and to connect and adjust them with an, e.g., obliquely located spindle 5. Thus, fixation of vertebral bones will always be possible in very many different injuries to the said vertebral bones W, as a result of which the chances of healing and the quality of healing are substantially improved.

Compared with the fixation of the said vertebral bones W that can be achieved with the band-like implant BI according to the state of the art, compression or distraction can be achieved with the said implant 1 according to the present invention, as a result of which the possible applications of an implant are substantially expanded. Moreover, the said implant can also be used as a holding aid instead of a surgical instrument that is normally additionally necessary, because it is able to hold the vertebrae in a position favorable for the operation during other surgical procedures.

In particular, the said two vertebral bones W can be adjusted very accurately in relation to one another by the said spindle 5, which is not possible in the case of the band-like implant according to the state of the art, because it does not provide a separate possibility of adjustment for the position of the said two vertebral bones W, since this position is determined by the mounting process, which can, in general, never be performed so accurately as a separate adjustment process in the case of the implant according to the present invention. It should be emphasized once again that the mounting of the said implant 1 according to the present invention can be performed without any preparation on the said vertebral bone W, as a result of which the operation time and consequently also the duration of anesthesia of the patient, on the one hand, as well as the size of the field of operation, i.e., the wound, on the other hand, can be reduced. Both represent substantial progress in the surgical treatment in operations which are critical in any event.

One essential advantage of the implant according to the present invention is the lateral arrangement of the said articulated bearing 4, which makes it possible to place this projecting component in a natural recess of the vertebral bone and consequently to avoid especially the hindering deformation of the esophagus.

While specific embodiments of the invention have been shown and described in detail to illustrate the application of the principles of the invention, it will be understood that the invention may be embodied otherwise without departing from such principles.

What is claimed is:

1. Device which can be fastened as an implant for a spinal column for fixing vertebrae, including fixing cervical vertebrae, on an anterior side, adjacent an esophagus, comprising:

a first kidney-shaped mounting plate, said first mounting plate being arched to not lie in a single plane, said first mounting plate having a ribbed surface on one side and having two holes for receiving fastening screws;

a second kidney-shaped mounting plate, said second mounting plate being arched to not lie in a single plane, said second mounting plate having a ribbed surface on one side and having two holes;

two fastening screws received by said two holes of said second mounting plate, said fastening screws for fastening said first mounting plate and said second mounting plate into a corresponding one vertebra and another vertebrae;

articulated bearing means connected to said first mounting plate and an articulated bearing means connected to said second mounting plate, each articulated bearing means being arranged on an end of an associated mounting plate, on a side opposite said ribbed surface for positioning the articulated bearing means adjacent the esophagus, upon fastening the associated mounting plate on an anterior side of a vertebra, each articulated bearing means including a bearing bush formed in one piece with said mounting plate, said bearing bush having a spindle hole extending essentially at right angles to a longitudinal extension of said mounting plate, including a bearing pin mounted in said bearing bush and movable therein;

a spindle provided with left-hand and right-hand threads with an angular shaft piece for actuating said spindle, said spindle engaging said bearing pin through said spindle hole of said articulated bearing means connected to said first mounting plate and engaging said bearing pin through said spindle hole of said articulated bearing means connected to said second mounting plate.

2. Device according to claim 1, wherein:
   said first kidney shaped mounting plate has a holding tab.

3. Device according to claim 2, wherein:

said bearing bush includes a cylindrical inner wall, and said bearing pin is inserted into said bearing bush.

4. Device according to claim 2, wherein:
said bearing bush includes a cylindrical inner wall and said bearing pin is a double truncated cone-shaped bearing pin, which is inserted into said bearing bush.

5. Device according to claim 2, wherein said two holes are located at different location along each said kidney-shaped mounting plate, offset in relation to one another in a vertical direction.

6. Device according to claim 1, wherein:
said bearing bush includes a cylindrical inner wall, and said bearing pin is inserted into said bearing bush.

7. Device according to claim 1, wherein:
said bearing bush includes a cylindrical inner wall and said bearing pin is a double truncated cone-shaped bearing pin, which is inserted into said bearing bush.

8. Device according to claim 1, wherein:
said spindle is permanently screwed with a free end into said bearing pin of said articulated bearing means connected to said first mounting plate.

* * * * *